(12) United States Patent
Gharbi et al.

(10) Patent No.: US 11,826,418 B1
(45) Date of Patent: Nov. 28, 2023

(54) VIRUS-LIKE PARTICLE (VLP)-BASED VACCINE AGAINST CVB4

(71) Applicant: KING FAISAL UNIVERSITY, Al-Ahsa (SA)

(72) Inventors: Jawhar Gharbi, Al-Ahsa (SA); Ikbel Hadj Hassine, Monastir (TN); Mohammed A. Almalki, Al-Ahsa (SA); Ameera Alyami, Al-Ahsa (SA); Manel Ben M'Hadheb, Monastir (TN)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/151,409

(22) Filed: Jan. 6, 2023

(51) Int. Cl.
| | |
|---|---|
| *A61K 39/00* | (2006.01) |
| *A61K 39/12* | (2006.01) |
| *A61K 39/125* | (2006.01) |
| *C07K 14/005* | (2006.01) |
| *C07K 14/085* | (2006.01) |
| *A61K 39/135* | (2006.01) |
| *A61K 9/00* | (2006.01) |
| *A61P 31/14* | (2006.01) |

(52) U.S. Cl.
CPC .......... *A61K 39/135* (2013.01); *A61K 9/0019* (2013.01); *A61P 31/14* (2018.01); *A61K 2039/5258* (2013.01); *A61K 2039/55555* (2013.01); *A61K 2039/6081* (2013.01)

(58) Field of Classification Search
CPC ............ A61K 2039/53; A61K 2039/70; A61K 39/12; A61K 39/125; C07K 14/005
See application file for complete search history.

(56) References Cited

U.S. PATENT DOCUMENTS 9,987,350 B2   6/2018   Cardosa et al.

FOREIGN PATENT DOCUMENTS

| CN | 11018242 B | 8/2021 |
|---|---|---|
| WO | 9953034 A1 | 10/1999 |

OTHER PUBLICATIONS

Georgilis et al., "Nanoparticles based on natural, engineered or synthetiv proteins and polypeptides for drug delivery applications", 2020, Int. Journal of Pharmceutics: 1-34.*
Hassine et al., "Characterization of Coxsackievirus B4 virus-like particles VLP produced by the recombinan baculo-virus-insect cell system expressing the major capsid protein" Molecular Biology Reports (2020), vol. 37, pp. 2835-2843 (Abstract only).

* cited by examiner

*Primary Examiner* — Barry A Chestnut
(74) *Attorney, Agent, or Firm* — Nath, Goldberg & Meyer; Richard C. Litman (57) ABSTRACT

The virus-like particle (VLP)-based vaccine against CVB4 infection includes a virus-like particle (VLP) derived from VP1 of Coxsackievirus B4 (CVB4). The vaccine is devoid of virus RNA. The virus-like particles may be in nanoparticle form and coated with a polymer coating. The polymeric coating may be albumin, e.g., bovine serum albumin (BSA).

7 Claims, 9 Drawing Sheets

Specification includes a Sequence Listing.

VIRUS-LIKE PARTICLE (VLP)-BASED VACCINE AGAINST CVB4

The instant application contains a Sequence Listing XML, which has been submitted in XML format via the USPTO's Patent Center and is hereby incorporated by reference in its entirety. The XML copy, created on Dec. 17, 2022, is named 32087_71U_SEQUENCE.xml and is 5,000 bytes in size.

BACKGROUND

1. Field

The disclosure of the present patent application relates to vaccines against CVB4 infection and, particularly, to a vaccine against CVB4 including a virus-like particle (VLP).

2. Description of the Related Art

Picornaviruses are a diverse family of viruses that cause a number of common illnesses. Of the Picornaviridae family, viruses of the genus Enterovirus, which are all very closely related, are significant for the number of diseases they cause.

Viruses of the genus Enterovirus affect millions of people worldwide each year, and are often found in the respiratory secretions (e.g., saliva, sputum, or nasal mucus) and stool of an infected person. Enterovirus infects the gut, thus the derivation of their name from the root "enteric". Historically, poliomyelitis was the most significant disease caused by an enterovirus, that is, poliovirus. There are 62 non-polio Enteroviruses that can cause disease in humans: 23 Coxsackie A viruses, 6 Coxsackie B viruses, 28 echoviruses, and 5 other enteroviruses. Polioviruses, as well as Coxsackie viruses and echoviruses, are spread through the fecal-oral route. Infection can result in a wide variety of symptoms, including mild respiratory illness (common cold), hand, foot and mouth disease, acute hemorrhagic conjunctivitis, aseptic meningitis, myocarditis, severe neonatal sepsis-like disease, and acute flaccid paralysis.

Enterovirus represents a genus of a large and diverse group of small RNA viruses characterized by a single positive-strand genomic RNA. All enteroviruses contain a genome of approximately 7,500 bases and are known to have a high mutation rate due to low-fidelity replication and frequent recombination. After infection of the host cell, the genome is translated in a cap-independent manner into a single polyprotein, which is subsequently processed by virus-encoded proteases into the structural capsid proteins and the nonstructural proteins, which are mainly involved in the replication of the virus.

The enteroviruses are associated with several human and mammalian diseases. Serologic studies have distinguished 66 human Enterovirus serotypes on the basis of antibody neutralization tests. Additional antigenic variants have been defined within several of the serotypes on the basis of reduced or nonreciprocal cross-neutralization between variant strains. On the basis of their pathogenesis in humans and animals, enteroviruses were originally classified into four groups, polioviruses, Coxsackie A viruses (CA), Coxsackie B viruses (CB), and echoviruses, but it was quickly realized that there were significant overlaps in the biological properties of viruses in the different groups.

Coxsackievirus B4 (CVB4), belonging to the Enterovirus genus, and the Picornaviridae family are considered environmental factors that have intrinsic capacity to damage the pancreatic beta cells, and thereby cause pancreatitis and Type 1 Diabetes in humans. Although vaccination against CVB4 could reduce the incidence of this chronic autoimmune disease, there is currently no therapeutic or vaccine in clinical use.

All picornaviruses share the same genomic structure, including four structural genes within the P1 gene: VP1, VP2, VP3, and VP4, wherein the VP4 and VP2 genes are expressed together as VP0, and viral proteases within the 3C and 3D genes. The viral protease can cleave the P1 gene, thereby allowing the virus to assemble into virus like particles (VLPs), virus capsomers, complexes and/or antigens of enteroviruses.

All members of the genus Enterovirus, including HEV71, polioviruses and Coxsackievirus A16, have a single-stranded positive sense RNA genome, which has a single open reading frame encoding a polyprotein, P1, consisting of the capsid proteins VP4, VP2, VP3 and VP1 and several non-structural proteins, including the viral proteases 3C and 3CD, which are responsible for cleaving the polyprotein P1 into individual capsid proteins VP1, VP3 and VP0, of which VP0 is eventually cleaved into VP2 and VP4. The capsid proteins may assemble into virus like particles (VLPs).

Thus, a virus-like particle (VLP)-based vaccine against CVB4 infection solving the aforementioned problems is desired.

SUMMARY

A virus-like particle (VLP)-based vaccine against CVB4 infection includes a virus-like particle (VLP) derived from VP1 of Coxsackievirus B4 (CVB4). The vaccine is devoid of virus RNA. The virus-like particle (VLP)-based vaccine may include a nanoparticle composition including VLP-VP1 and a polymeric coating encapsulating VLP-VP1. The polymeric coating can comprise albumin, e.g., bovine serum albumin (BSA).

A method of vaccinating a subject against a human Coxsackievirus B4 (CVB4) infection may include administering to the subject the virus-like particle (VLP)-based vaccine against CVB4 infection as described herein in an amount effective to elicit an immune response and/or neutralizing antibody response directed against the human CVB4 infection when administered to the subject.

The molecular characteristics and morphology of VLP-VP1 are the same as the wild-type virus particles except that the VLPs do not include virus RNA genome. As such, the VLPs do not cause viral multiplication in cells, tissues and host and do not induce pancreatic damage that is associated with the wild-type virus strain. The VLP-VP1 has been shown to generate a high level of neutralizing protective antibodies in animal sera.

These and other features of the present subject matter will become readily apparent upon further review of the following specification and drawings.

BRIEF DESCRIPTION OF THE DRAWINGS

in FIGS. 4D, 4E, and 4F infected HighFive cells; and in FIGS. 4G, 4H, and 4I zoom 3× of infected HighFive cells.

FIGS. 7A-7D are micrographs of murine pancreas tissues stained with hematoxylin and eosin from: in FIG. 7A, a mouse inoculated with wild-type CVB4; in FIG. 7B, a control uninfected mouse; in FIG. 7C, a mouse inoculated with VLP product at 10 days post immunization; and in (FIG. 7D, a mouse inoculated with VLP product at 28 days post immunization.

FIGS. 14A-14D are micrographs showing pancreas tissues stained with haematoxylin and eosin from: in FIG. 14A, control challenged mice group; in FIG. 14B, mice group immunized with VP1-VLP vaccine and challenged; in FIG. 14C, mice group immunized with VP1-VLP-NP vaccine and challenged; and in FIG. 14D, naive non challenged mice group.

Similar reference characters denote corresponding features consistently throughout the attached drawings.

DETAILED DESCRIPTION OF THE PREFERRED EMBODIMENTS

The following definitions are provided for the purpose of understanding the present subject matter and for construing the appended patent claims.

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

The term, "subject," as used herein, refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

It will be understood that the term "Virus-Like Particle", or (VLP), is a term well known to those of ordinary skill in the art in the field of immunology and in the field of pharmaceuticals, being defined as molecules that closely resemble viruses, but are noninfectious because they contain no viral genetic material for replicating. VLPs have been used in pharmaceutics as a delivery system or carrier for genes and other therapeutics. VLPs have also been used in vaccines, since they present viral surface proteins that are viral epitopes that may elicit strong T-cell and B-cell immune system responses.

The virus-like particle (VLP)-based vaccine against Coxsackievirus B4 (CVB4) infection includes a virus-like particle (VLP) derived from VP1 of Coxsackievirus B4 (CVB4). The virus-like particle VLP derived from VP1 of Coxsackievirus B4 (CVB4) is referred to herein as VLP-VP1. VLP-VP1 can be produced by expressing the wild-type major capsid protein VP1 in a eukaryotic system. The Coxsackievirus B4 (CVB4) strain may be the Coxsackievirus B4-E2 (CVB4-E2) strain. The vaccine is devoid of virus RNA.

VP1 is the immunodominant capsid protein of all the serotype strains belonging to the Enterovirus genus and the family of Picornaviridae. As described herein, the present inventors have found that VLP-VP1 is effective to elicit an immune response and/or a neutralizing antibody response directed against CVB4 when administered to a subject. Accordingly, the virus-like particle (VLP)-based vaccine against Coxsackievirus B4 (CVB4) does not include virus-like particles derived from capsid proteins other than VP1. VLP-VP1 is sufficient to elicit an immune response and/or a neutralizing antibody response directed against CVB4. The present inventors have further discovered that VLP-VP1 nanoparticles, e.g., VLP-VP1 nanoparticles including a polymeric coating (VLP-VP1-NP), can elicit a significantly higher immune response in a subject than that achieved by VLP-VP1 without the polymeric coating.

The virus-like particle (VLP)-based vaccine may include a nanoparticle composition including VLP-VP1 and a polymeric coating, referred to herein as polymeric VLP-VP1 nanoparticles, or "VLP-VP1-NP". The VLP-VP1 nanoparticles may have a particle size ranging from about 1 nm to about 100 nm. The polymeric coating can comprise albumin, e.g., bovine serum albumin (BSA). Albumin has been shown to be stable across various pH ranges, is highly soluble, and is biodegradable. Any suitable process for encapsulating the VLP-VP1 within the polymeric coating can be used. The process of encapsulation may include spray drying, in which a solution including VLP-VP1 and the polymer is aerosolized to create droplets that are briefly heated to evaporate water and then cooled to produce the desired spray-dried particulates.

The virus-like particle (VLP)-based vaccine against Coxsackievirus B4 (CVB4) infection may include a suitable adjuvant. For example, the VLP-VP1 or VLP-VP1-NP may be combined with any suitable adjuvant, such as Modified Vaccinia Virus, ISCOMS, alum, aluminum hydroxide, aluminum phosphate, or any other suitable adjuvant.

The molecular characteristics and morphology of the VLPs are the same as the wild-type virus particles, except that the VLPs do not include virus RNA genome. As such, the VLPs do not cause viral multiplication in cells, tissues and host and do not induce pancreatic damage that is associated with the wild-type virus strain. The VLPs have been shown to generate a high level of neutralizing protective antibodies in animal sera.

A method of vaccinating a subject against CVB4 infection, e.g., a diabetogenic coxsackievirus B4-E2 (CVB4-E2) strain infection, may include administering to the subject the virus-like particle (VLP)-based vaccine in an amount effective to elicit an immune response and/or neutralizing antibody response directed against CVB4 when administered to the subject. The vaccine may be administered intraperitoneally, for example.

As described herein, the present inventors have found that the vaccine produced viral pseudo-particles when tested in a mice model and successfully conferred protection for the mice by the production of protective antibodies in the sera.

The virus-like particle (VLP)-based vaccine against Coxsackievirus B4 (CVB4) may induce a protective immune response. The term "protective immune response" and/or "neutralizing immune response", as used herein, is intended to mean that the vaccinated subject may resist or protect itself against an infection with the pathogenic agent against which the vaccination was done.

The VLPs can be produced by expressing the recombinant major capsid protein rVP1 of Coxsackievirus B4 in a suitable eukaryotic system. For example, a CVB4 VLP expression cassette may be contained in a recombinant virus, which may transfect the host cell. Suitable viruses that may be used for this purpose include baculovirus, vaccinia, sindbis virus, SV40, Sendai virus, retrovirus and adenovirus. Suitable host cells may include host cells that are compatible with the above viruses, and these include insect cells such as *Spodoptera frugiperda* (e.g. Sf9 cells) *Trichoplusia ni*, CHO cells, chicken embryo fibroblasts, BHK cells, human SW13 cells, *drosophila*, and mosquito cells derived from *Aedes albopictus*.

Figure 1:
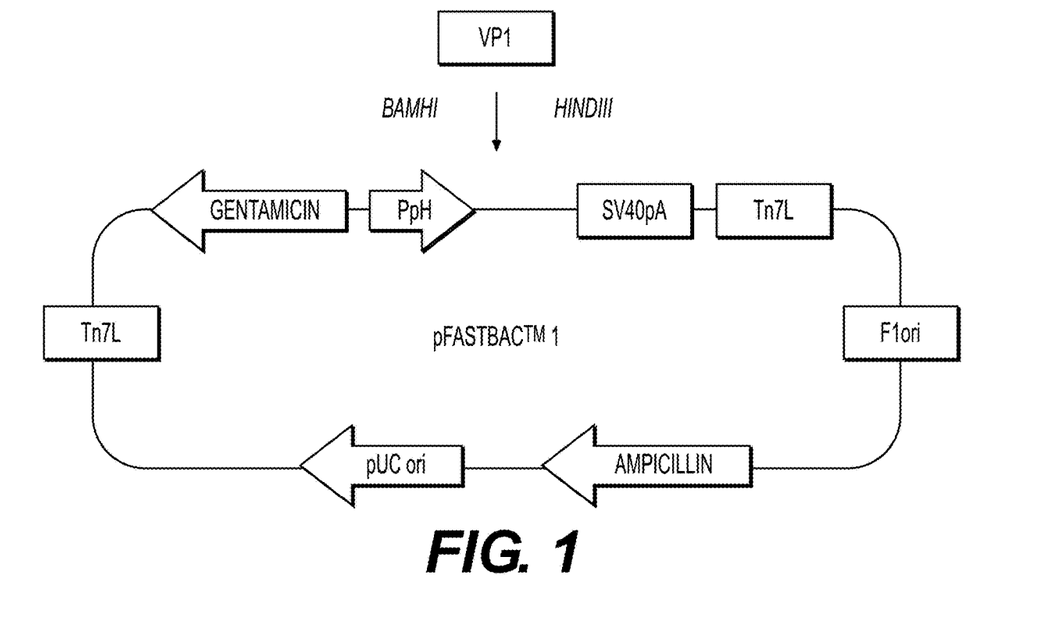
FIG. 1 is a schematic diagram of the recombinant plasmid, showing the VP1 sequence (SEQ ID NO:2) placed between the site of restriction enzymes BamHI and HindIII of the pFastBac™1 vector.
Figure 2:
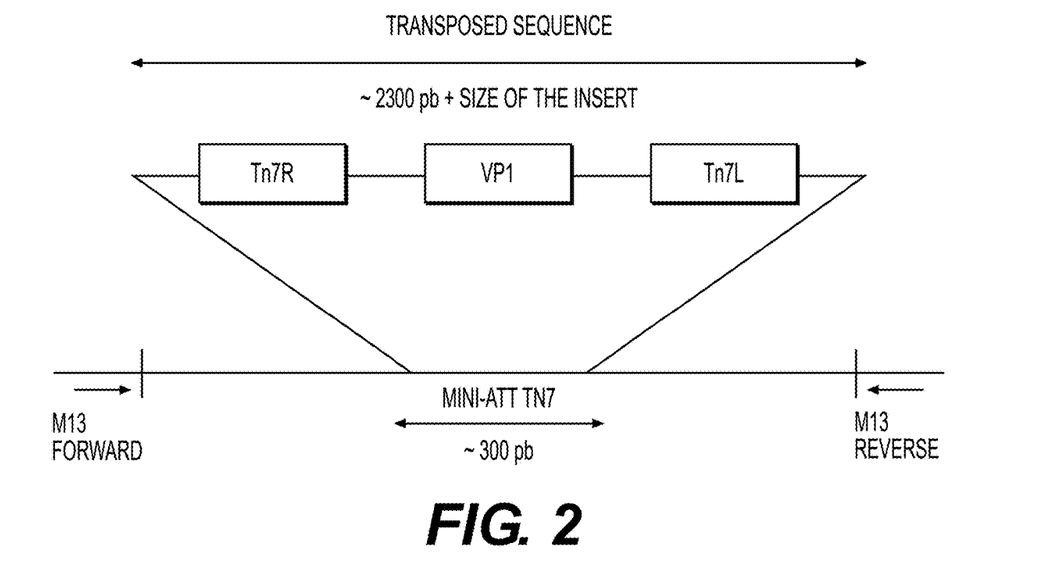
FIG. 2 is a diagram of VP1 and the complete transposed sequence (SEQ ID NO:1), flanked by Tn7 elements in the bacmid, and flanked by the priming sites of the M13 forward and reverse primers.

As shown in FIGS. 1 and 2, the CVB4 VLP cassette can be cloned into a pFastBac™1 baculoviral transfer vector and transposed into a bacmid. FIG. 1 is a schematic presentation of the recombinant plasmid, showing the VP1 sequence (SEQ ID NO: 2) placed between the site of restriction enzymes BamHI and HindIII of the pFastBac1 vector. FIG. 2 shows VP1 and the complete transposed sequence (SEQ ID NO: 1), flanked by Tn7 elements in the bacmid, which are flanked by the priming sites of the M13 forward and reverse primers. The resulting VLP product retains the same molecular and morphological characteristics of the wild-type virus particles when examined by Western blot (FIG. 3), immunofluorescence imaging (FIGS. 4A-4I), and electron microscopy (FIG. 5).

Figure 3:
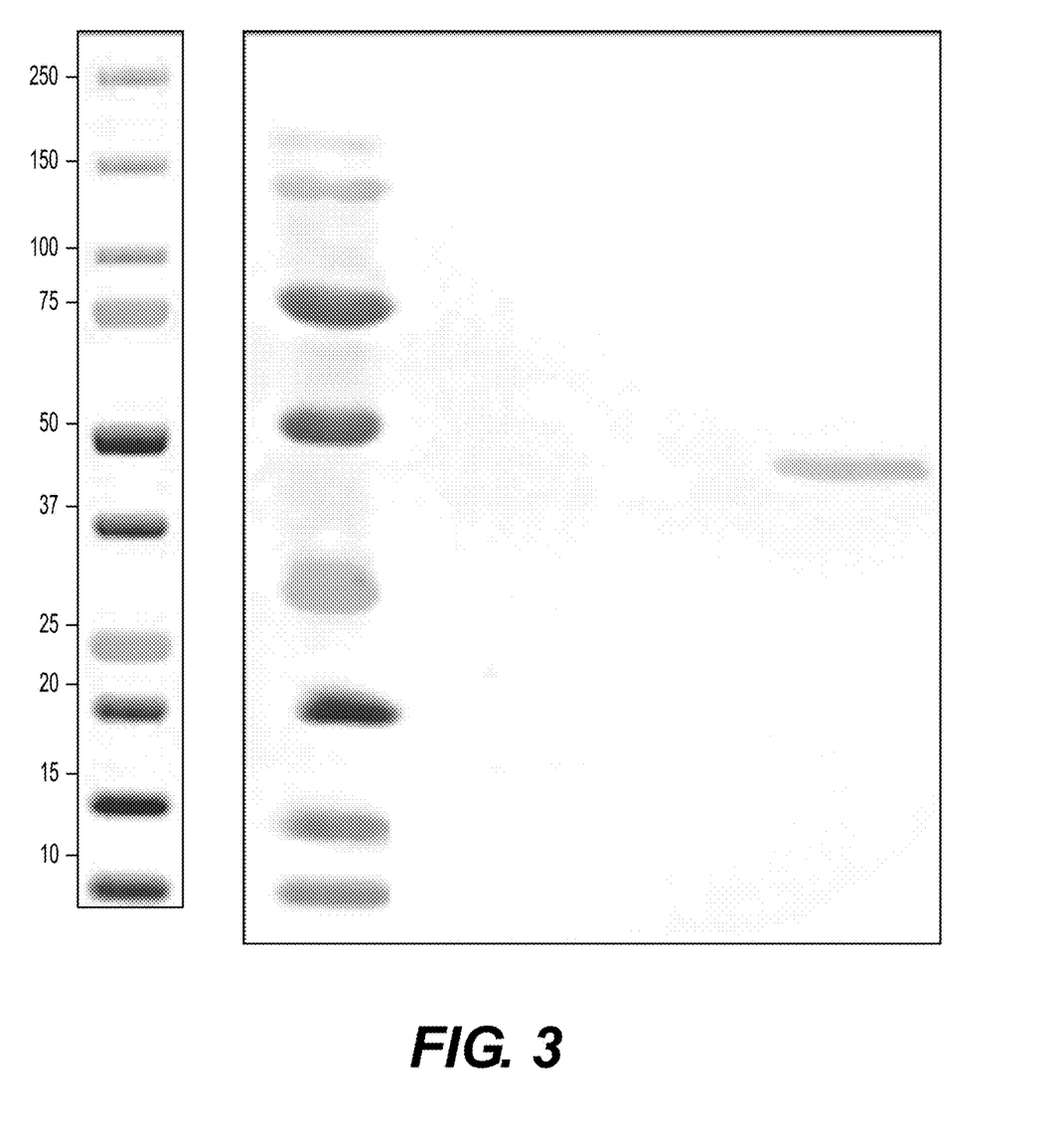
FIG. 3 is a Western blot showing media containing free viruses.

The Western blot analysis shown in FIG. 3 depicts media containing free viruses. The viral stock of Bac-VP1 (rVP1) is demonstrated in the last lane with ~30 KD of weight, compared to the molecular weight (10-250 KD) used in the first lane.

Figure 4A:
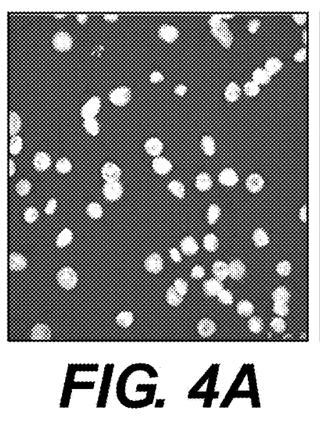
FIGS. 4A-4I are immunofluorescence (IF) micrographs including in FIGS. 4A, 4B, and 4C non-infected HighFive cells.
Figure 4B:
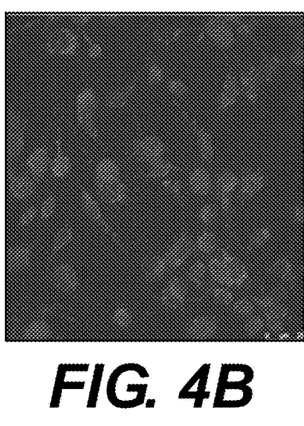
Figure 4C:
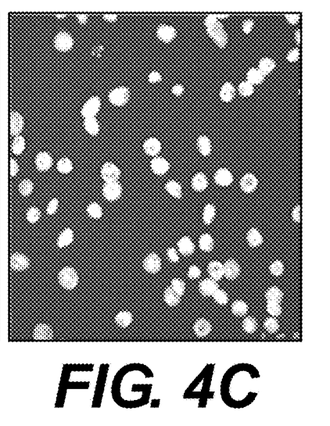
Figure 4D:
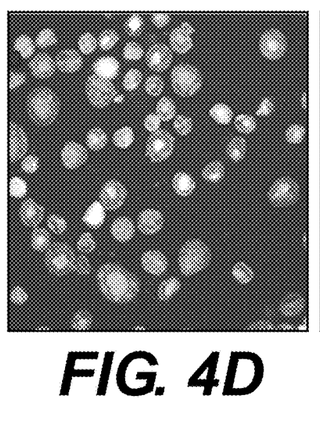
Figure 4E:
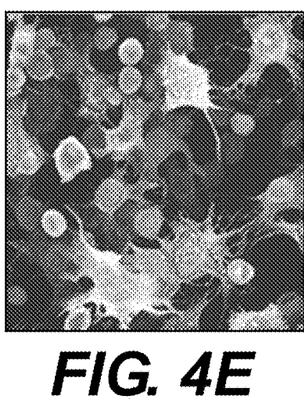
Figure 4F:
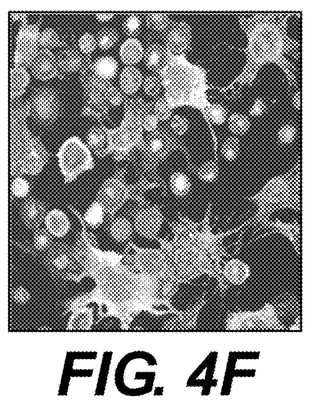
Figure 4G:
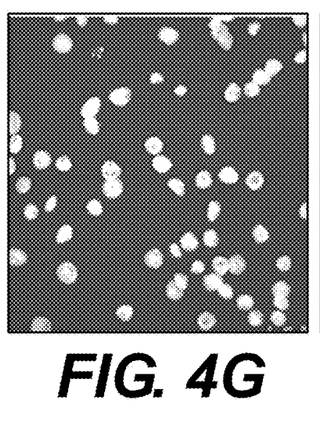
Figure 4H:
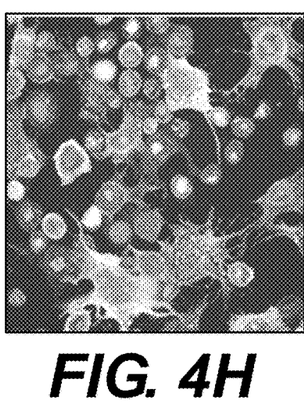
Figure 4I:
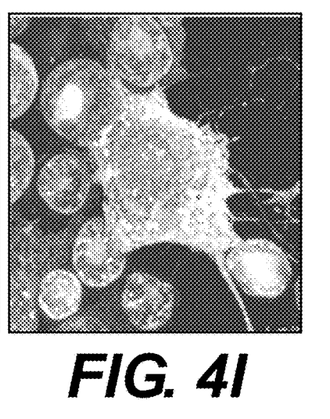

For the immunofluorescence (IF) microscopy used to detect rVP1, at 2 days post infection, HighFive cell cultures (infected and non-infected) were fixed and processed for IF using a mouse anti-Enterovirus monoclonal antibody, followed by incubation with goat anti-mouse coupled to AlexaFluor 488. Nuclei were stained with DAPI. Merge immunofluorescence was obtained using ADOBE PHOTOSHOP, and cells were visualized by confocal laser scanning microscopy (CLSM). Fluorescence signals were recorded separately by using appropriate filters. The presented images correspond to confocal sections showing non-infected High-Five cells (FIGS. 4A-4C), infected HighFive cells (FIGS. 4D-4F) and zoom 3× of the infected cells (FIGS. 4G-4I).

Figure 5:
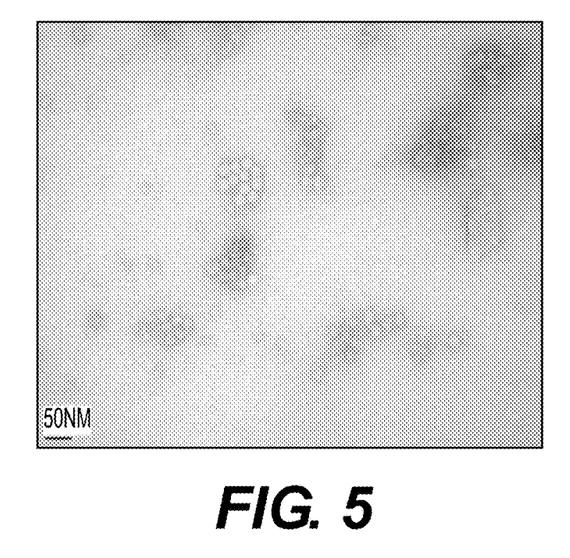
FIG. 5 is an electron micrograph of the purified CVB4 VLPs (expressed by the baculovirus-insect cell system) visualized using electron microscopy (Bars, 50 nm).

FIG. 5 depicts the purified CVB4 VLPs (expressed by the baculovirus-insect cell system) visualized using electron microscopy (Bars, 50 nm).

Figure 6:
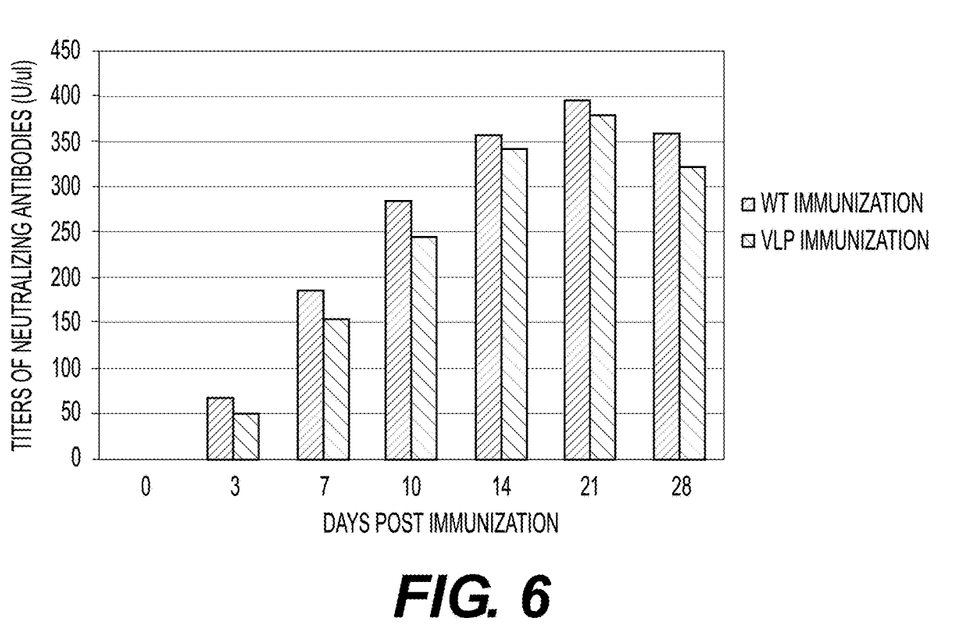
FIG. 6 is a chart comparing the evolution of the anti-CVB4 neutralizing and protective antibodies after immunization by the VLP product and by the wild-type (WT) JBV strain of CVB4 (administered by intraperitoneal routes) from day 0 to day 28 after immunization.
Figure 7A:
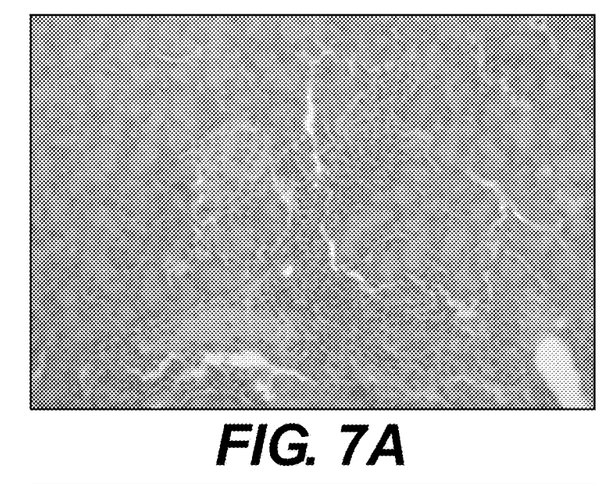
Figure 7B:
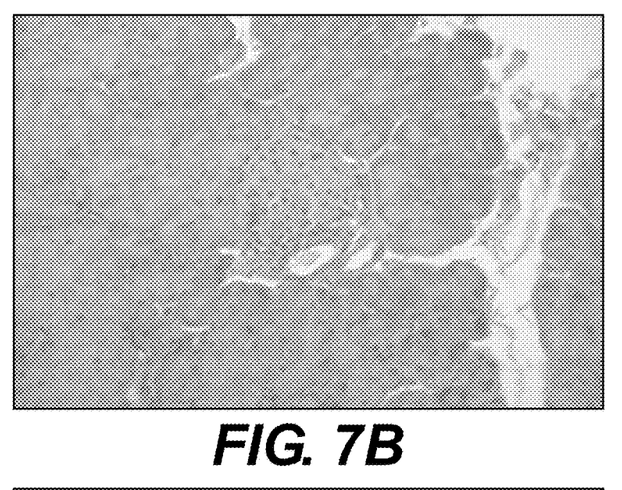
Figure 7C:
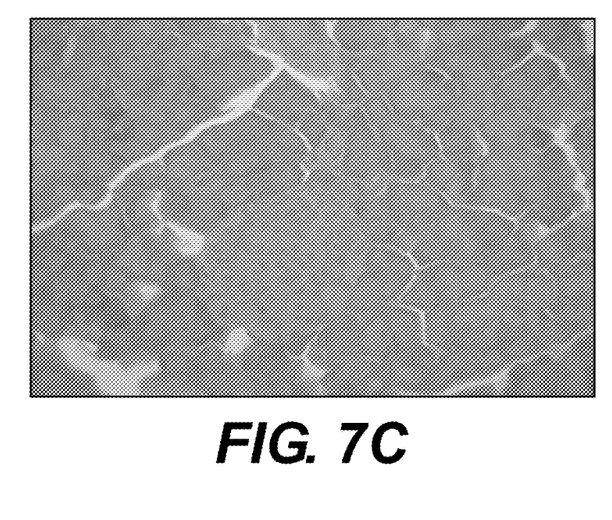
Figure 7D:
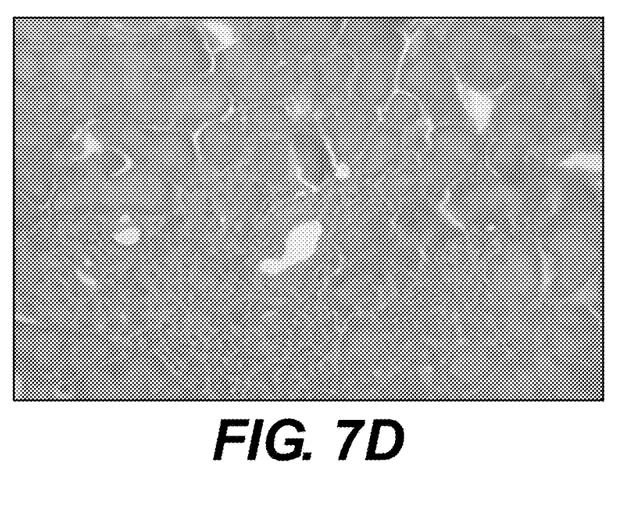
Figure 8:
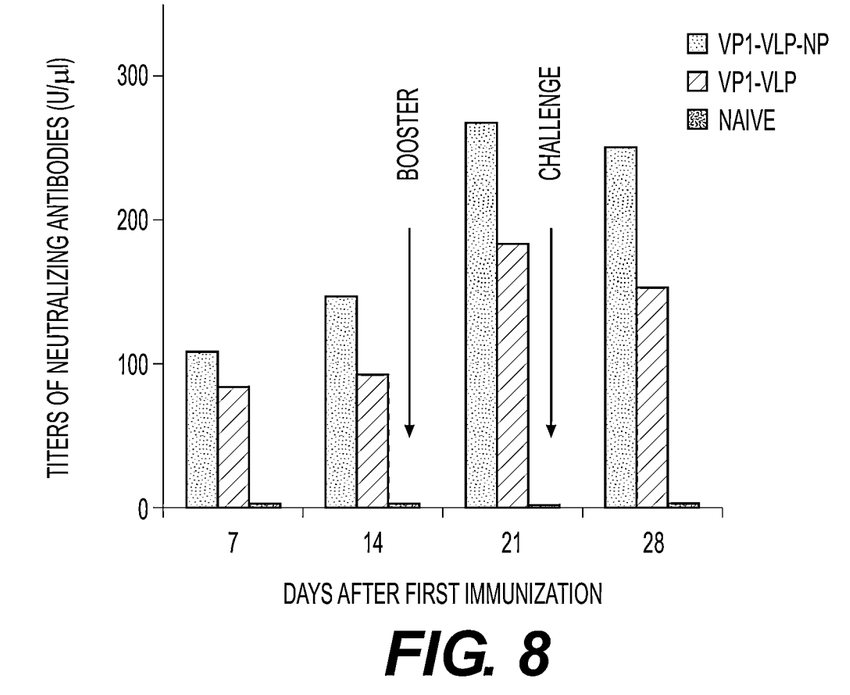
FIG. 8 is a chart comparing IgG levels of mice receiving experimental VP1-VLP-NP vaccine with mice immunized by VP1-VLP and control mice.
Figure 9:
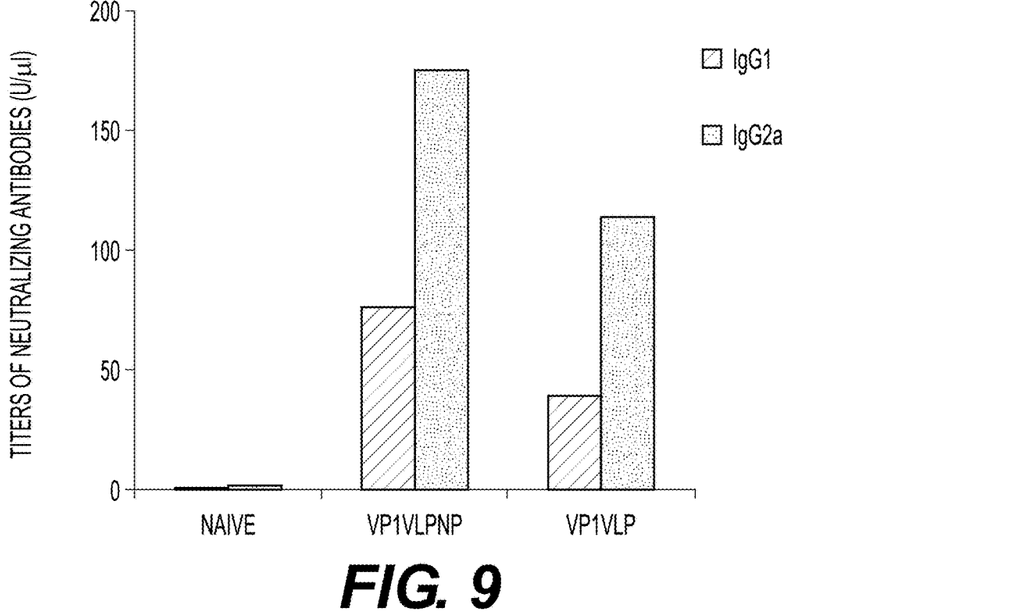
FIG. 9 is a chart comparing levels of IgG2a antibodies in the serum of mice immunized with VP1-VLP-NP with the serum of mice immunized with VP1-VLP and control mice.
Figure 10:
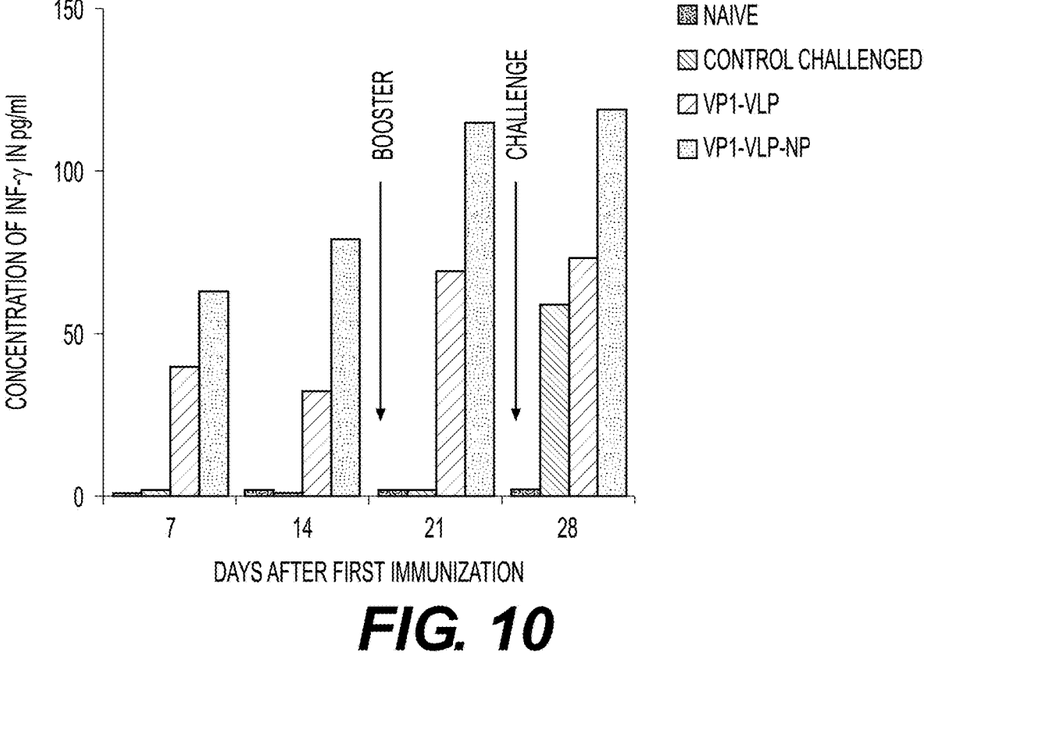
FIG. 10 is a chart comparing interferon (IFN-γ) levels in the VP1-VLP-NP immunization group with the VP1-VLP immunization group and the control naive group.
Figure 11:
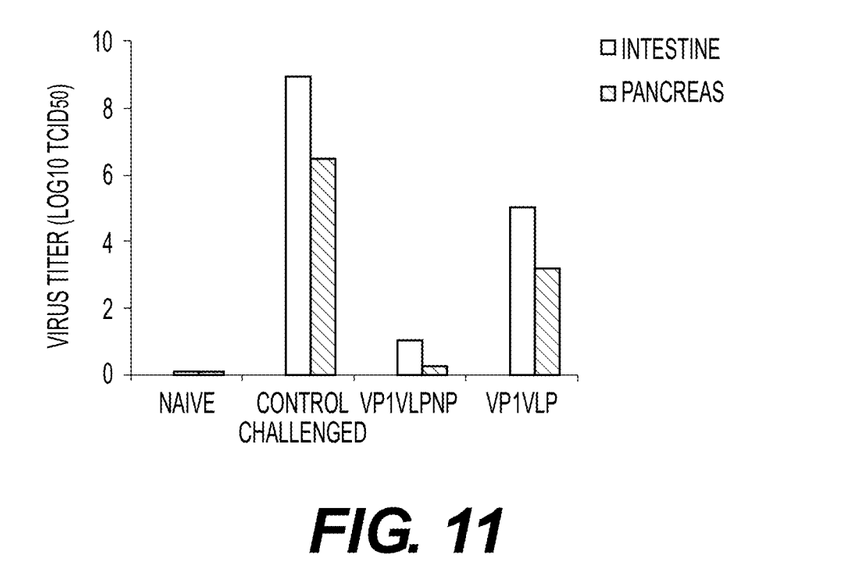
FIG. 11 is a chart comparing the viral titer of wild-type virus in the pancreas and intestine of mice immunized with VP1-VLP-NP with mice immunized with VP1-VLP and with control mice.
Figure 12:
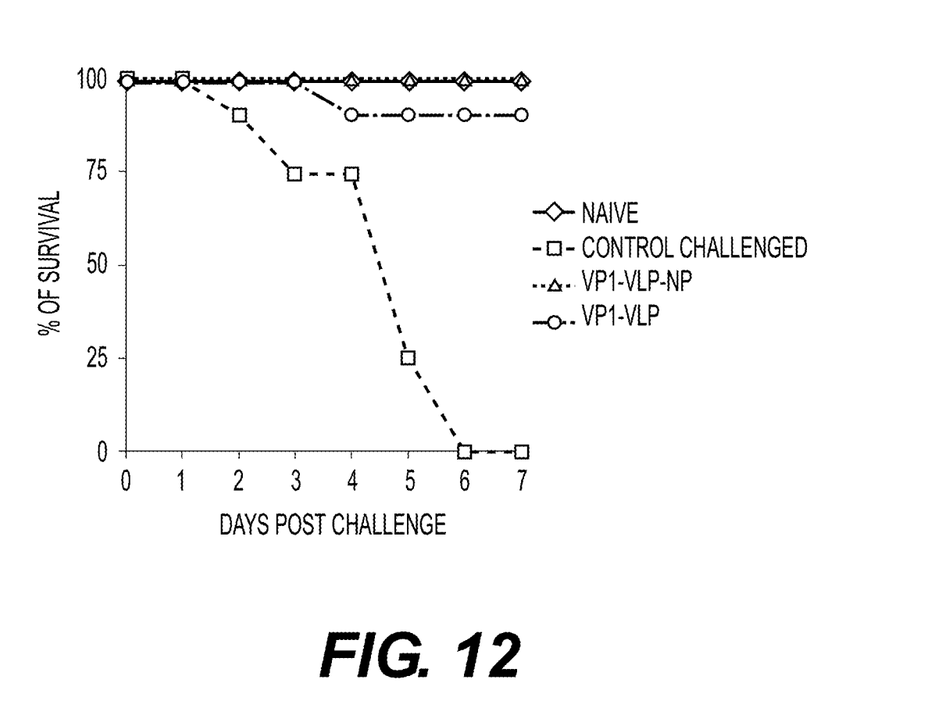
FIG. 12 is a graph comparing survival of mice groups immunized with VP1-VLP vaccine, naïve mice, control mice, and mice immunized with VP1-VLP-NP.
Figure 13:
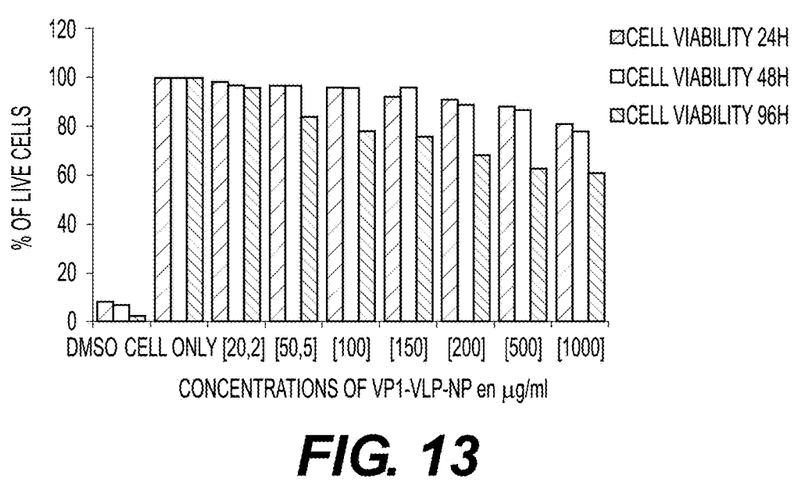
FIG. 13 is a chart showing in vitro cell cytotoxicity of VP1-VLP-NP vaccine determined by evaluating metabolically active (live) treated cells with different concentrations of VP1-VLP-NP for short-term (14 and 48 h) and long-term (96 h) cytotoxicity.
Figure 14A:
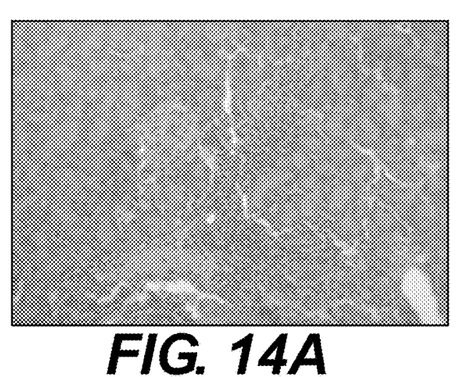
Figure 14B:
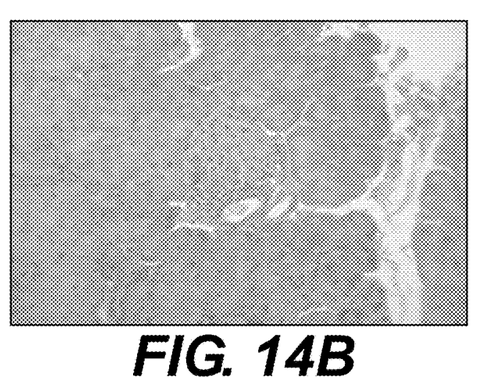
Figure 14C:
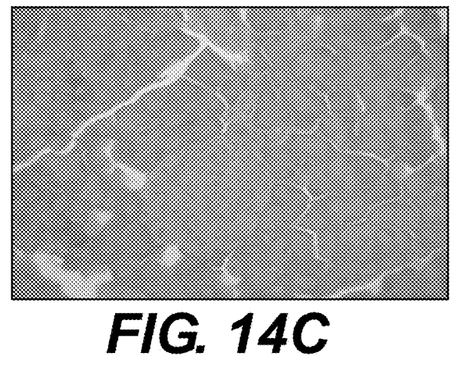
Figure 14D:
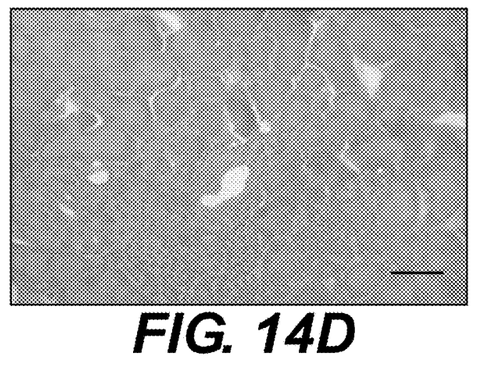

The engineered CVB4 VLPs do not induce damage in pancreatic tissues. In experiments, mice inoculated with the engineered CVP4 VLPs did not suffer any damage to pancreatic tissues. Further, a high level of neutralizing protective antibodies in mice sera compared to the wild-type virus was achieved post-immunization, the neutralizing activity being induced by the engineered CVB4 VLPs. FIG. 6 depicts the evolution of the anti-CVB4 neutralizing and protective antibodies after immunization by the VLP product or by the wild-type (WT) JBV strain of CVB4 (administered by intraperitoneal routes) from day 0 to day 28 after immunization. The sera was serially diluted 1:10 to determine the highest dilution capable of completely inhibiting the cytopathic effect of the CVB4 wild-type.

FIGS. 7A-7D depict murine pancreas tissue of Swiss mice after being immunized with engineered CVB4 VLPs or wild-type viruses. The murine pancreas tissues were stained with hematoxylin and eosin from a mouse inoculated with wild-type CVB4 (FIG. 7A), from a control uninfected mouse (FIG. 7B), from a mouse inoculated with VLP product at 10 days post immunization (FIG. 7C), and from a mouse inoculated with VLP product at 28 days post immunization (FIG. 7D).

It was further found that VP1-VLP-NP vaccine produced significantly higher IgG levels compared to mice immunized by VP1-VLP. Mice were immunized intraperitoneally (IP) with VP1-VLP or VP1-VLP-NP with a boost regimen at days 0 and 15. Neutralizing antibody IgG levels and concentrations of cytokine INF-γ were measured by ELISA and micro-neutralization assays in serum collected from mice at days 7, 14, 21 and 28. Mice were challenged at day 22 by the diabetogenic wild-type CVB4-E2 strain with a dose of $4.25\times10^4$ TCID50). All mice groups except naive mice were challenged by the diabetogenic wild-type CVB4-E2 strain at day 22. As shown in FIG. 8, results showed that mice receiving experimental VP1-VLP-NP vaccine produced significantly higher IgG levels compared to mice immunized by VP1-VLP. The experimental vaccine containing VP1 using polymeric Nanoparticle (VP1-VLP-NP) was shown to induce higher levels of anti-VP1-specific antibodies than vaccine containing VP1 alone (VP1-VLP).

Total IgG subclass titers showed strong correlation with the experimental vaccine used in passive immunization. Isotypes of IgG, IgG1 and IgG2a were evaluated seven days (day 7) after challenge by the wild-type CVB4-E2 strain. As shown in FIG. 9, IgG2a antibodies were elevated more in the serum of mice immunized with VP1-VLP-NP than in serum of mice immunized with VP1-VLP. The mice group immunized by VP1-VLP-NP and challenged by the wild-type strain showed increased levels of Th1 (Lymphocytes T helper) related subclass IgG2a compared to mice immunized by VP1-VLP. Naive control mice illustrated very low titers compared to all other groups.

Interferon (IFN-γ) was measured to determine whether VP1-VLP-NP or VP1-VLP could elicit cellular immunity. The concentrations of IFN-γ in serum of mice groups immunized by VP1-VLP-NP or VP1-VLP and naive mice group were examined by ELISA assay. As shown in FIG. 10, results showed that the interferon (IFN-γ) levels in the VP1-VLP-NP immunization group increased significantly compared with VP1-VLP immunization group and control naive group, inducing effective cellular immunity in mice.

Cytokine levels in vaccinated mice were determined by collecting serum from mice groups immunized with VP1-VLP-NP or VP1-VLP and from naive mice at days 7, 14, 21 and 28 days after the first immunization. The concentrations of IFN-γ were calculated in μg/ml by ELISA method. As shown in FIG. 11, viral titer of wild-type virus was shown to be ~40-fold lower in the pancreas and intestine of mice immunized with VP1-VLP-NP compared to mice immunized with VP1-VLP. As expected, the viral load in the control challenged mice group was considerably high.

Mortality of Swiss albino mice was determined as indication of virulence of the infection. Titer calculation was made on HeLa cell culture of the wild-type virus isolated seven days (day 7) post challenge from mice organs. HeLa cells were plated at a density of $1\times10^6$ cells. Intestine and pancreas homogenates were collected from all immunized groups and used as viral stock samples and added to the cells. The viral titers are expressed as tissue cell infectious dose/ml ($TCID_{50}$) in FIG. 12. Naive mice received PBS. However, control challenged mice received only the wild-type strain dose at challenge day 22. After 7 days post challenge by the wild-type CVB4-E2 strain, all control challenged mice showed complete lethality of the group (100% mortality). Results revealed a small decrease of survival mice (10%) for mice group immunized with VP1-VLP vaccine. All other groups of naive not challenged mice and mice immunized with VP1-VLP-NP vaccine showed no mortality.

The In vitro cell cytotoxicity of VP1-VLP-NP vaccine was determined by evaluating metabolically active (live) treated cells with different concentrations of VP1-VLP-NP for short-term (14 and 48 h) and long-term (96 h) cytotoxicity. Results revealed that for VP1-VLP-NP, cell viability was not concentration-dependent after treatment for 24 and 48 h, with all nanoparticle concentrations demonstrating cell viabilities of at least 72% (FIG. 13). The 500 μg/ml and 1000 μg/ml concentrations did not result in a significant reduction in cell viability compared to cell control. After 96 h exposure to VP1-VLP-NP, cell viability was concentration-dependent, demonstrating decreased cell viability with higher concentrations of nanoparticles. Cell viability for all VP1-VLP-NP concentrations at 96 h was lower than control cells.

Various concentrations of VP1-VLP-NP nanoparticles ranging from 20.2 to 1000 μg/mL and 10 μL DMSO were used to treat cells. Cells only (with no treatment) were used as control. Each cell-containing well ($1\times10^6$ cells) received 100 μl of particle suspension. For short-term cytotoxicity, the cells were treated for 24 h and 48 h, whereas for long-term cytotoxicity, the cells were treated for 96 h. After the incubation period, the cells were washed with PBS and MTT reagent was added. Metabolically active (live) cells were evaluated by reading OD at 570 nm. The average absorbance of the cells-only group (untreated) was set as 100% cell viability. Passive immunization with VP1-VLP-NP vaccine was found to better protect Swiss albino mice from virus-induced pancreas tissue damage than the immunization with VP1-VLP vaccine. As shown in FIGS. 14A-14D, microscopic examination of pancreas tissue showed no inflammatory damage in mice immunized with VP1-VLP-NP vaccine. Pancreas tissue appeared normal and indistinguishable from pancreas tissue of naive control mice. Pancreas tissue from mice group immunized with VP1-VLP revealed mild inflammation. As expected, the wild-type CVB4-E2 virus strain provoked widespread inflammatory lesions and necrosis area (pancreatitis) in pancreas tissue of control challenged mice. Histology of Swiss albino mice pancreas was taken seven days (day 7) after challenge with the wild-type virus strain. Mice groups were immunized at days 0 and 15 with VP1-VLP-NP and VP1-VLP vaccines, and then challenged at day 22 with the wild-type CVB4-E2 strain. Shown are pancreas tissue stained with haematoxylin and eosin from the control challenged mice group (FIG. 14A), from the mice group immunized with VP1-VLP vaccine and challenged (FIG. 14B), from the mice group immunized with VP1-VLP-NP vaccine and challenged and (FIG. 14C) from the naive non challenged mice group (FIG. 14D) (Bars, 200 μm).

The present teachings will be better understood with reference to the following examples.

Example 1

VP1-VLP-Loaded BSA Polymeric Nanoparticles (VP1-VLP-NP)

Spray drying was used to form VP1-VLP-NPs. Spray drying is an easy and rapid process of encapsulation, in which an antigen-polymer solution is aerosolized to create droplets that are briefly heated to evaporate the water and then cooled to produce desired spray-dried particulates.

Twenty (20) mg of BSA (Bovine Serum Albumin) were cross-linked with 6 μl of glutaraldehyde in 25 ml deionized water overnight under magnetic stirring to form a polymer solution. Albumin has been shown to be stable across various pH ranges, is highly soluble, and is biodegradable. Excess glutaraldehyde in the solution was neutralized by the addition of 2 mg of 1M sodium bisulfite. Finally, 250 μl of Tween 80 was added to the polymer solution. Under magnetic stirring, a suspension containing 1 mg of previously produced VP1-VLP was added dropwise to the polymer solution.

Using a Spray Dryer, the polymer solution with the VP1-VLP product was sprayed at 120° C. using compressed air. The spray-drying process involves atomization through forcing a fluid through an outlet that creates a spray, including droplets of a desired size. Moisture from produced droplets was removed after atomization by drying to form spray-dried VP1-VLP-BSA polymeric nanoparticles (VP1-VLP-BSA-polymeric NPs).

It is to be understood that the virus-like particle (VLP)-based vaccine against Coxsackievirus B4 (CVB4) infection is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A virus-like particle (VLP)-based vaccine against Coxsackievirus B4 (CVB4) infection, comprising a nanoparticle composition including a virus-like particle (VLP) derived from viral protein VP1 (VP1) of Coxsackievirus B4 (CVB4) and a polymeric coating encapsulating the virus-like particle (VLP).

2. The virus-like particle (VLP)-based vaccine against Coxsackievirus B4 (CVB4) as recited in claim 1, wherein the polymeric coating comprises albumin.

3. The virus-like particle (VLP)-based vaccine against Coxsackievirus B4 (CVB4) as recited in claim 2, wherein the polymeric coating comprises bovine serum albumin (BSA).

4. The virus-like particle (VLP)-based vaccine against Coxsackievirus B4 (CVB4) as recited in claim 1, wherein the nanoparticle composition has a particle size of about 1 nm to about 100 nm.

5. A virus-like particle (VLP)-based vaccine against Coxsackievirus B4 (CVB4) infection, comprising a virus-like particle (VLP) derived from viral protein VP1 (VP1) of Coxsackievirus B4 (CVB4), the virus-like particle (VLP) being a nanoparticle encapsulated in a polymeric coating.

6. The virus-like particle (VLP))-based vaccine against Coxsackievirus B4 (CVB4) infection as recited in claim 5, wherein the polymeric coating comprises albumin.

7. The virus-like particle (VLP))-based vaccine against Coxsackievirus B4 (CVB4) infection as recited in claim 5, wherein the polymeric coating comprises bovine serum albumin (BSA).

* * * * *

SEQUENCE LISTING

```
Sequence total quantity: 2
SEQ ID NO: 1            moltype = DNA   length = 861
FEATURE                 Location/Qualifiers
source                  1..861
                        mol_type = genomic DNA
                        organism = Coxsackievirus B4 (CVB4)
SEQUENCE: 1
ttttatcaag ggccaacaga ggaatctgtg gagcgagcaa tgggtagggt tgcagatacc   60
attgccagag gtccatcaaa ctccgagcag atccctgcct taacggctgt ggaaactggg  120
cacacttctc aagtagaccc tagtgacact atgcaaacaa gacatgtgca caattaccac  180
tcaaggtcag agtcatctat agaaaacttc ttatgcaggt ctgcatgtgt gatttatata  240
aaatattcta gtgctgaatc aaacaacttg aagcgctatg cagaatgggt cattaataca  300
agacaagtgg cgcagttgcg gcggaagatg gaaatgttca cctacattcg ttgtgacatg  360
gaacagacat ttgtcatcac tagtcatcaa gagatgtcca ctgccactaa ctctgtcgtt  420
ccagtccaaa cacatcaaat aatgtacgtg ccacctggtg gtcccgtacc aacatcagtt  480
aatgattatg tgtggcaaac gtccaccaac cctagcatct tctggacaga gggcaacgca  540
ccaccgagaa tgtcaatacc attcatgagc ataggtaatg cgtacaccat gttctatgac  600
ggttggtcga atttttccag ggacggcata tatggctaca attcactgaa caatatgggg  660
accatttacg cacgccatgt taacgattct agtccaggag ggttgaccag caccatccgc  720
atctacttta aacccaagca tgtaaaggcg tacgtgcgcc caccgcgccg cttgtgccaa  780
tacaagaaag ccaagaacgt gaattttgat gttgaggctg tcaccaccga gcgtgcaagt  840
ctggtaacca ctggacctca t                                            861

SEQ ID NO: 2            moltype = DNA   length = 868
FEATURE                 Location/Qualifiers
source                  1..868
                        mol_type = genomic DNA
                        organism = Coxsackievirus B4 (CVB4)
SEQUENCE: 2
gaagggcccg gagggagggg ggtgcatggg tagggttgca gcaaccctct gcccagtcca   60
tcaaactccg agcagatccc tgccctaacg gctgtggaaa ctgggcacac ttctcaagta  120
gaccctagtg acactatgca aacaagacat gtgcacaatt accactcaag gtcagagtca  180
tcaatagaaa acttcttatg caggtctgca tgtgtgattt aatgtcagag tcatcaaata  240
gaaaacttct tatgcaggtt ctgcatgtgt gatttatata aaatatctag tgctgaatca  300
aacaacttga agcgctatgc agaatgggtc atttttttct ttgtttttgt ggcgcagttg  360
cggcggaaga tggatatgtt cacatacatt cgttgtgaca tggaactgac atttgtcatc  420
actagtcatc aagagatgtc cactgccact aactctgacg ttccagtcca aacacatcaa  480
ataatgtacg tgccacctgg tggtcccgta ccaacatcag ttaatgatta tgtgtggcaa  540
acgtccacca accctagcat attctggaca gagggcaacg caccaccgag aatgtcaata  600
ccattcatga gcataggtaa tgcgtacacc atgttctatg acgttggtc gaatttttcc  660
agggacggca tatatggcta caattcactg aacaatatgg gaccatttta cgcacgccat  720
```

-continued

```
gttaacgatt ctagtccagg agggttgacc agcaccatcc gcatctactt taaacccaag    780
catgtaaagg cgtacgtgcc gcgcccaccg cgcttgtgtc aatacaagaa agccaagaac    840
ggaatttgat gtgaggcttc accaccat                                       868
```